US008526575B1

(12) United States Patent
Lyon et al.

(10) Patent No.: US 8,526,575 B1
(45) Date of Patent: Sep. 3, 2013

(54) COMPOUND X-RAY LENS HAVING MULTIPLE ALIGNED ZONE PLATES

(75) Inventors: Alan Francis Lyon, Berkeley, CA (US); Michael Feser, Walnut Creek, CA (US); Wenbing Yun, Walnut Creek, CA (US); Sharon Chen, San Ramon, CA (US)

(73) Assignee: Xradia, Inc., Pleasanton, CA (US)

( * ) Notice: Subject to any disclaimer, the term of this patent is extended or adjusted under 35 U.S.C. 154(b) by 294 days.

(21) Appl. No.: 12/855,463

(22) Filed: Aug. 12, 2010

Related U.S. Application Data

(60) Provisional application No. 61/233,375, filed on Aug. 12, 2009.

(51) Int. Cl.
*G21K 1/00* (2006.01)
(52) U.S. Cl.
USPC ............. 378/145; 378/43; 378/70; 378/205
(58) Field of Classification Search
USPC ...................... 378/43, 70, 145, 205
See application file for complete search history.

(56) References Cited

U.S. PATENT DOCUMENTS

| | | | | |
|---|---|---|---|---|
| 3,882,310 | A * | 5/1975 | Barrett | 378/2 |
| 3,906,229 | A * | 9/1975 | DeMeester et al. | 250/336.1 |
| 5,424,549 | A | 6/1995 | Feldman | |
| 5,744,059 | A * | 4/1998 | Yamashita et al. | 252/299.61 |
| 5,926,318 | A * | 7/1999 | Hebert | 359/618 |
| 5,946,281 | A * | 8/1999 | Ito et al. | 369/112.07 |
| 6,269,145 | B1 * | 7/2001 | Piestrup et al. | 378/81 |
| 6,917,472 | B1 | 7/2005 | Yun et al. | |
| 7,057,187 | B1 | 6/2006 | Yun et al. | |
| 7,072,442 | B1 | 7/2006 | Janik | |
| 7,365,909 | B2 * | 4/2008 | Yun et al. | 359/565 |
| 7,440,546 | B2 * | 10/2008 | Liu et al. | 378/85 |
| 2009/0168187 | A1 * | 7/2009 | Woodgate et al. | 359/623 |

OTHER PUBLICATIONS

Di Fabrizio, F, et al., "Nano-optical elements fabricated by e-beam and x-ray lithography," Nano- and Micro-Optics for Information Systems, Proceedings of SPIE, 2003, pp. 113-125, vol. 5225.
Divan, R., et al., "Progress in the Fabrication of High-Aspect-Ratio Zone Plates by Soft X-ray Lithography," Design and Microfabrication of Novel X-Ray Optics, Proceedings of SPIE, 2002, pp. 82-91, vol. 4783.

(Continued)

*Primary Examiner* — Thomas R Artman
(74) *Attorney, Agent, or Firm* — Houston & Associates, LLP

(57) ABSTRACT

A compound zone plate comprising a first zone plate frame including a first zone plate, a second zone plate frame including a second zone plate, and a base frame to which the first zone plate frame and the second zone plate frame are bonded. In examples, two more zone plates are added to make a four element optic. In the assembly process, the microbeads are used to ensure the parallelism, dial in the distance precisely between the zone plates by selecting the microbead size, possibly in response to the width of the frames, and ensure low friction lateral movement enabling nanometer precision alignment of the zone plates with respect to each other prior to being fixed by the adhesive. That is, when the frames are pressed together to ensure parallelism, it is still possible to align them to each other since the microbead layer facilitates the inplane movement of the alignment process.

19 Claims, 13 Drawing Sheets

(56) References Cited

OTHER PUBLICATIONS

Kuyumchyan, A., et al., "High efficiency and low absorption Fresnel compound zone plates for hard X-ray focusing," Design and Microfabrication of Novel X-Ray Optics, Proceedings of SPIE, 2002, pp. 92-96, vol. 4783.

Peuker, M., et al., "High resolution phase zone plates for water window wavelengths," X-Ray Microfocusing: Applications and Techniques, Proceedings of SPIE, 1998, pp. 118-128, vol. 3449.

Shastri, S.D., et al., "Microfocusing of 50 keV undulator radiation with two stacked zone plates," Optics Communications, Sep. 15, 2001, pp. 9-14, vol. 197.

Spector, S.J., et al., "Process optimization for production of sub-20 nm soft x-ray zone plates," Journal of Vacuum Science and Technology B, Nov. 1997, pp. 2872-2876, vol. 15, No. 6.

Werner, S., et al., "Towards stacked zone plates," Journal of Physics: Conference Series, 2009, 3 pages, vol. 186, IOP Publishing.

Wieland, M., et al., "Zone-plate interferometry at 13 nm wavelength," Applied Physics B Lasers and Optics, 2003, pp. 885-889, vol. 76.

Wilhein, T., et al., "Differential interference contrast x-ray microscopy," Soft X-Ray and EUV Imaging Systems II, Proceedings of SPIE, 2001, pp. 163-171, vol. 4506.

\* cited by examiner

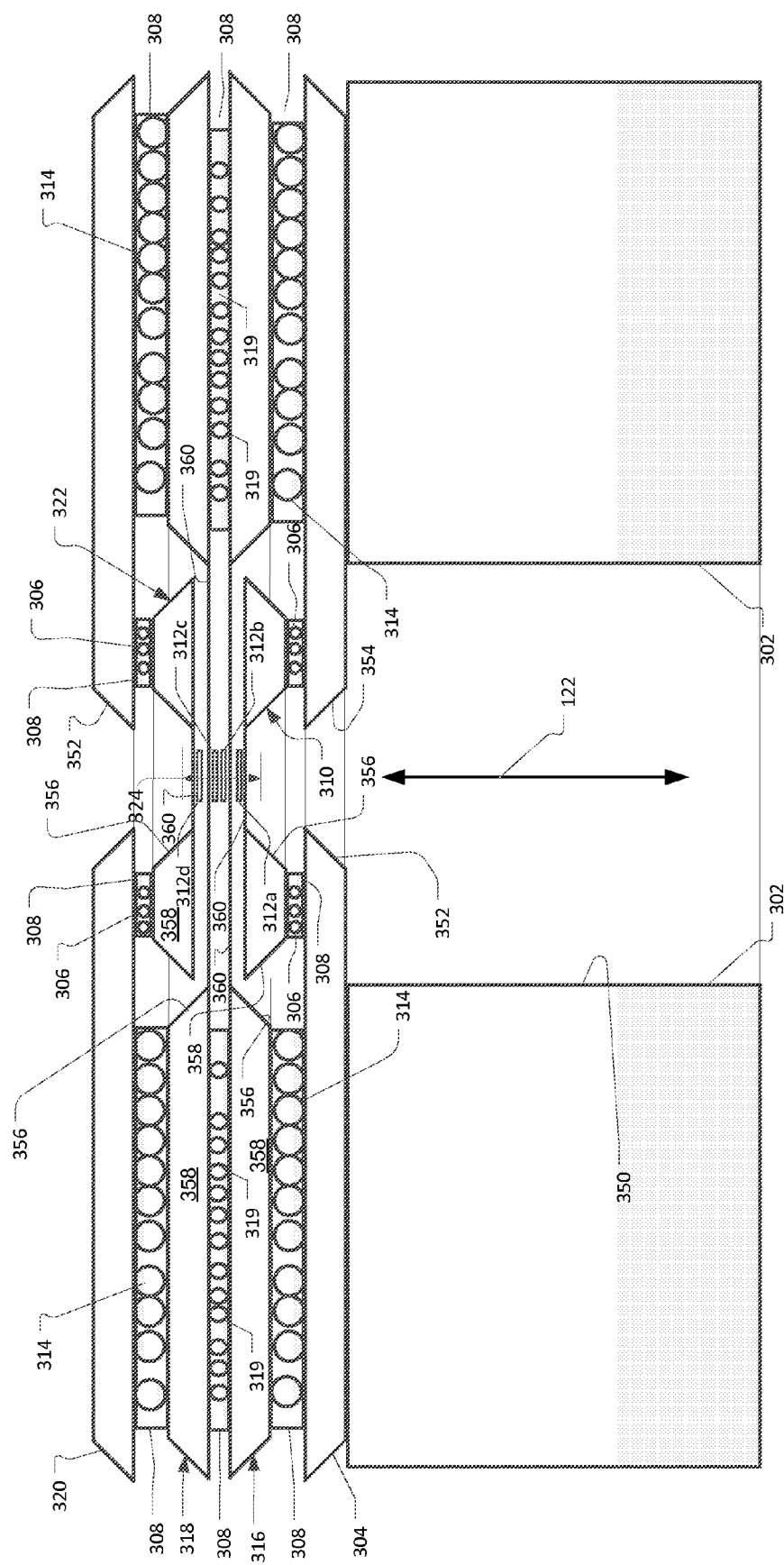

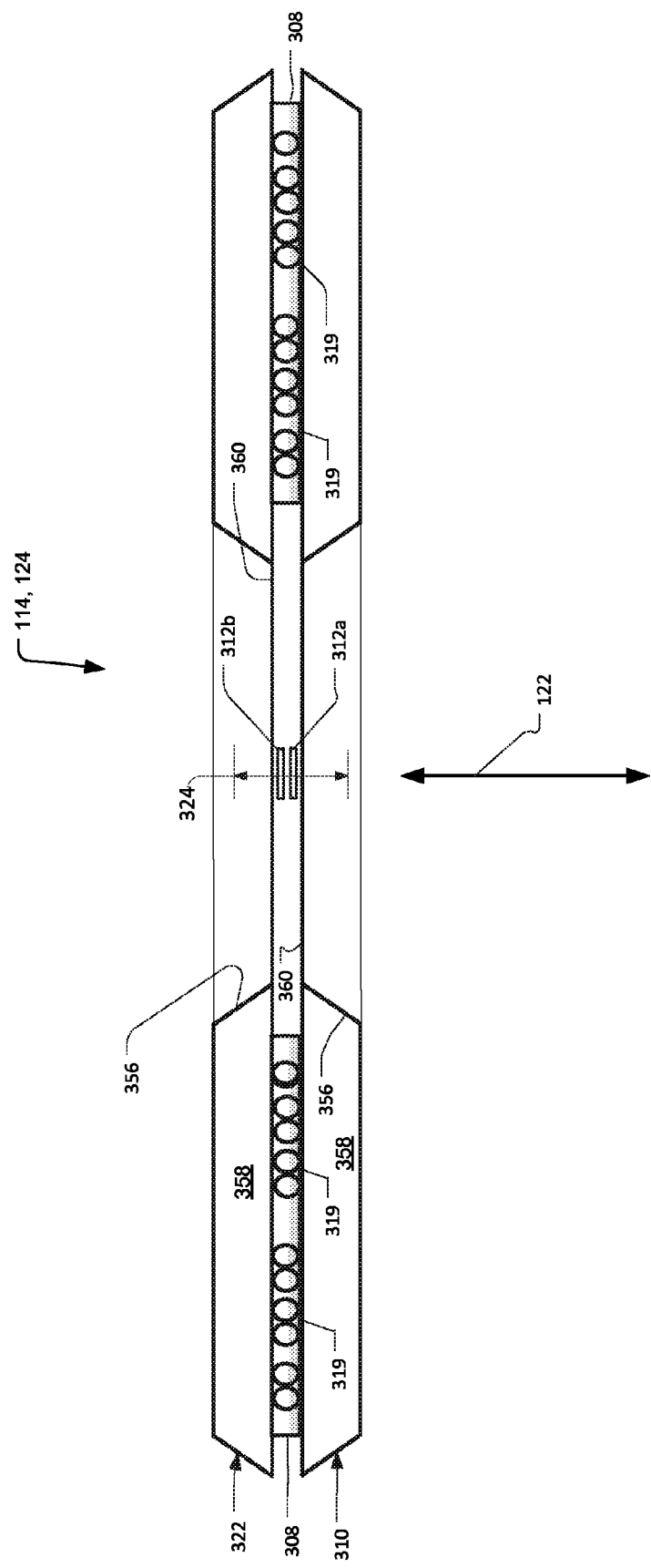

FIG. 8
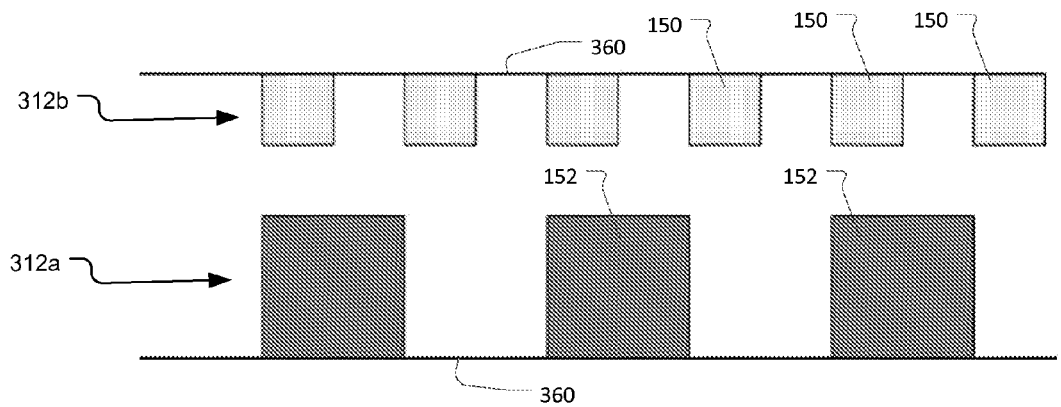
FIG. 9
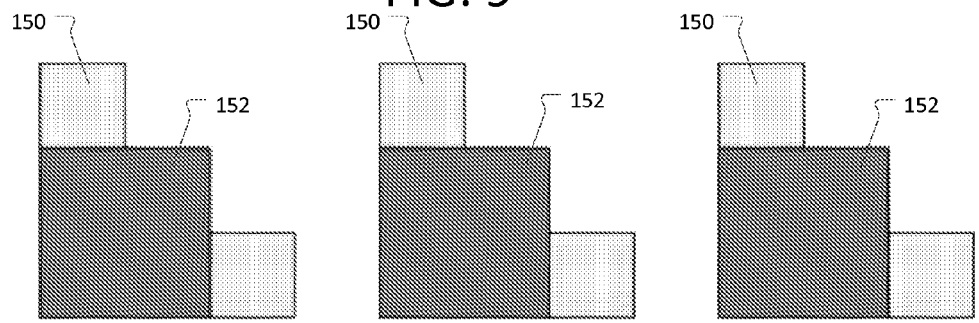
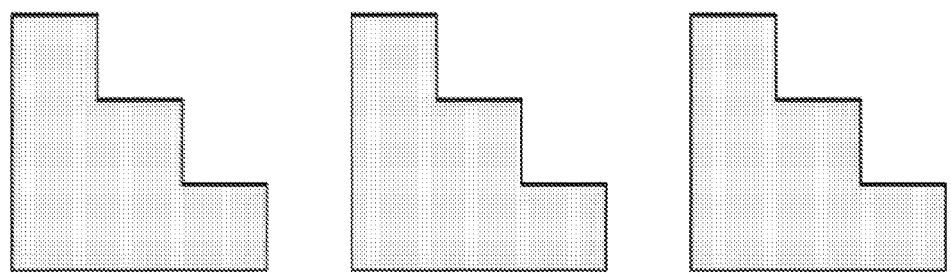

COMPOUND X-RAY LENS HAVING MULTIPLE ALIGNED ZONE PLATES

RELATED APPLICATIONS

This application claims the benefit under 35 USC 119(e) of U.S. Provisional Application No. 61/233,375, filed on Aug. 12, 2009, which is incorporated herein by reference in its entirety.

BACKGROUND OF THE INVENTION

Lens-based high-resolution x-ray microscopy largely resulted from research work at synchrotron radiation facilities in Germany and United States starting in the 1980's. While projection-type x-ray imaging systems with up to micrometer resolution have been widely used since the discovery of x-ray radiation, ones using x-ray lens with sub-100 nanometer (nm) resolution began to enter the market only this century. These high-resolution microscopes are configured similarly to visible-light microscopes with an optical train typically including an x-ray source, condenser, objective lens, and detector.

Because x rays do not refract significantly in most materials, nearly all such x-ray microscopes use diffractive objective lenses, called Fresnel zone plates. As illustrated in FIG. 1, they are essentially circular diffraction gratings, with the grating spacing decreasing with increasing distance from the center in order to increase the diffraction angle and thus produce the focusing effect. By year 2009, x-ray microscopes using synchrotron x-ray sources have achieved 30 nm resolution and commercial systems using laboratory x-ray sources have achieved 50 nm resolution.

Compared with the widely used visible light and electron microscopy techniques, x-ray microscopy combines properties that make it favorable for a large number of applications: (1) high energy x rays have very large penetration length to image internal structures of a thick samples without deprocessing; (2) the absorption and fluorescence emission depends strongly on the elemental composition of the sample, allowing high-sensitivity material analysis; and (3) x-ray imaging causes little structural damage to integrated circuit samples without a charging effect.

The key component of an x-ray microscope is the zone plate lens that focuses the x-rays and magnifies the x-ray images. From FIG. 2, the diffraction-limited resolution of the zone plate lens z is $\delta=1.22\Delta r_n$, the focal length is $f=2 r_n/(\lambda\Delta r_n)$, and the numerical aperture is $NA=\lambda/(2\Delta r_n)$. Zone plates with zones intended primarily to block x-ray radiation are called amplitude zone plate. They can provide up to 9% efficiency. Zone plate with zones intended to produce an ideally $\pi$ phase shift are called phase zone plates. They can provide up to 40% efficiency. In practice, a zone plate will both absorb and phase shift the x-ray beam impinging on it, and will behave as a combination of amplitude and phase zone plates. Even higher theoretical efficiency can be achieved when the zones approximate the profile of a Fresnel lens. This type of "blazed" zone plates can achieve nearly 100% theoretical efficiency.

The efficiency depends primarily on the wavelength and the thickness of the zones. An amplitude zone plate reaches its maximum efficiency when each zone completely absorbs the x-ray beam; and a phase zone plate reaches its maximum efficiency when each zone shifts the phase of x-ray beam by $\pi$, with no absorption. For example, with higher x-ray energy, the zone thickness must be increased to maintain absorption or phase shift.

Thinner zone plates are generally acceptable when using soft x-ray energies within the range of 200-500 eV. However, in order to image inorganic materials such as that used in material science research or semiconductors industries, the x-ray energy must be increased to multi-keV range in order to penetrate samples without excessive deprocessing.

FIG. 3 is a plot of efficiency as a function of x-ray energy for different gold zone plate thicknesses. With higher energy x-ray radiation, thicker zone plates are required to achieve its optimal efficiency. For example, a zone plate having a thickness of 1650 nanometers (nm) reaches a maximum efficiency at just below 10 keV. At this same energy, a 350 nm thick zone plate has an efficiency below 5%. Therefore, the challenge of making high resolution and high efficiency zone plate lenses becomes the challenge of making structures with high thickness-to-width aspect ratio, especially with increasing x-ray energy. For zone plates with 50 nm outer zone width, this would require an aspect ratio of 33. Such a high aspect ratio often poses significant difficulty for fabricating a single optic element.

The criticality in fabricating thicker zone plates comes in the fabrication and the mechanical stabilization of the outer zones. It is here that the aspect ratios become extreme since the outer zones are the narrowest zones, yet have to be the same height as the other, inner, wider zones. Fabricating these zones challenges existing fabrication processes such as plating technology due to the narrowness of the zones. And then, once fabricated, those high aspect ratio zones can be easily toppled by mechanical stress or other stresses due to charging effects.

Some have proposed to fabricate effectively thick zone plates by aligning and stacking separate zone plates to create a compound optic. One specific example relies on the formation of a zone plate doublet by fabricating two zone plates on either side of a common substrate. This approach is problematic, however, because it necessitates thin substrates and front side and backside alignment and fabrication. Moreover, the first fabricated zone plate must survive the fabrication process for the second zone plate. Another approach relies on the fabrication of a series of zone plates successively, one on top of the other. In such approach, however, tolerances stacked up. It further requires effective planarization prior to forming the next zone plate along with techniques for stabilizing the zones sufficiently to survive multiple planarization processes.

Nevertheless, compound x-ray optical elements have been developed. U.S. Pat. No. 6,917,472 B1 describes an Achromatic Fresnel Optic (AFO). This is typically a two element compound optic that is comprised of a diffractive Fresnel zone plate and a one or more refractive Fresnel lenses. Generally, AFO's have been proposed for imaging short wavelength radiation including extreme ultraviolet (EUV) and x-ray radiation. The diffractive element is the primary focusing element, and the refractive element typically provides no or very little net focusing effect. It serves to correct the chromatic aberration of the zone plate.

SUMMARY OF THE INVENTION

This invention pertains to methods to fabricate compound x-ray lenses including two or more zone plate lenses. In these compound lenses, the individual zone plates are placed in proximity along the longitudinal direction and aligned preferably to an accuracy better than the outer most zone width $\Delta r_n$. The resulting compound lens maintains the resolution of individual zone plates but lead to greatly increased focusing efficiency.

In general, according to one aspect, the invention features a compound zone plate comprising a first zone plate frame including a first zone plate, a second zone plate frame including a second zone plate, and a base frame to which the first zone plate frame and the second zone plate frame are bonded.

In embodiments, a spacer is used between the first zone plate frame and the base frame. Further, the second zone plate frame comprises a membrane, the second zone plate fabricated on the membrane, and an optical port to the membrane, in which the first zone plate is positioned laterally within the optical port. A third zone plate frame comprising a third zone plate and possibly a fourth zone plate can be further bonded to the assembly.

In general, according to another aspect, the invention features compound zone plate comprising a first zone plate frame including a first zone plate, a second zone plate frame including a second zone plate, and a spacer between the first zone plate frame and the second zone plate frame including microbeads and possibly an adhesive.

In the assembly process, the microbeads are used to ensure the parallelism, dial in the distance precisely between the zone plates by selecting the microbead size, possibly in response to the width of the frames, and ensure low friction lateral movement enabling nanometer precision alignment of the zone plates with respect to each other prior to being fixed by the adhesive. That is, when the frames are pressed together to ensure parallelism, it is still possible to align them to each other since the microbead layer facilitates the inplane movement of the alignment process.

In one embodiment, a third zone plate frame including a third zone plate is bonded to the second zone plate frame via a base frame.

In general, according to another aspect, the invention features a method for fabricating a compound zone plate comprising placing a first zone plate frame comprising a first zone plate over a second zone plate frame comprising a second zone plate, placing microbeads and an adhesive mechanically between the first zone plate frame and the second zone plate frame, and aligning the first zone plate to the second zone plate prior to hardening of the adhesive.

In the current embodiment, the step of aligning the first zone plate to the second zone plate comprises transmitting x-rays through the first zone plate and the second zone plate and detecting the x-rays and positioning the first zone plate relative to the second zone plate in response to the detected x-rays.

Preferably the x-rays are detected with a spatially resolved detector. The position is performed to optimize a Moiré pattern on the detector. Also additional zone plates are attached at similarly actively aligned, in one example.

In general, according to still another aspect, the invention features full-field x-ray imaging system including an x-ray source that generates an x-ray beam, a sample stage for holding a sample in the x-ray beam, a compound zone plate optic including a first zone plate frame comprising a first zone plate, a second zone plate frame comprising a second zone plate that is bonded to the first zone plate frame, and a spatially resolved detector system that detects the x-ray beam from the sample and the compound zone plate optic.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, the same or similar reference characters refer to the same parts throughout the different views. The drawings are not necessarily to scale; emphasis has instead been placed upon illustrating the principles of the invention. Of the drawings:

FIG. 5A is a side cross-sectional view of a compound zone plate that has been constructed according to aspects of the present invention;

FIG. 5B is a side cross-sectional view of a compound zone plate according to another embodiment;

FIG. 8 illustrates the configuration of successive zone plates to yield a blazed 4-level stacked compound zone plate lens;

FIG. 9 illustrates the effective zone profile produced from the blazed 4-level stacked compound zone plate lens.

DETAILED DESCRIPTION OF THE PREFERRED EMBODIMENTS

Figure 1:
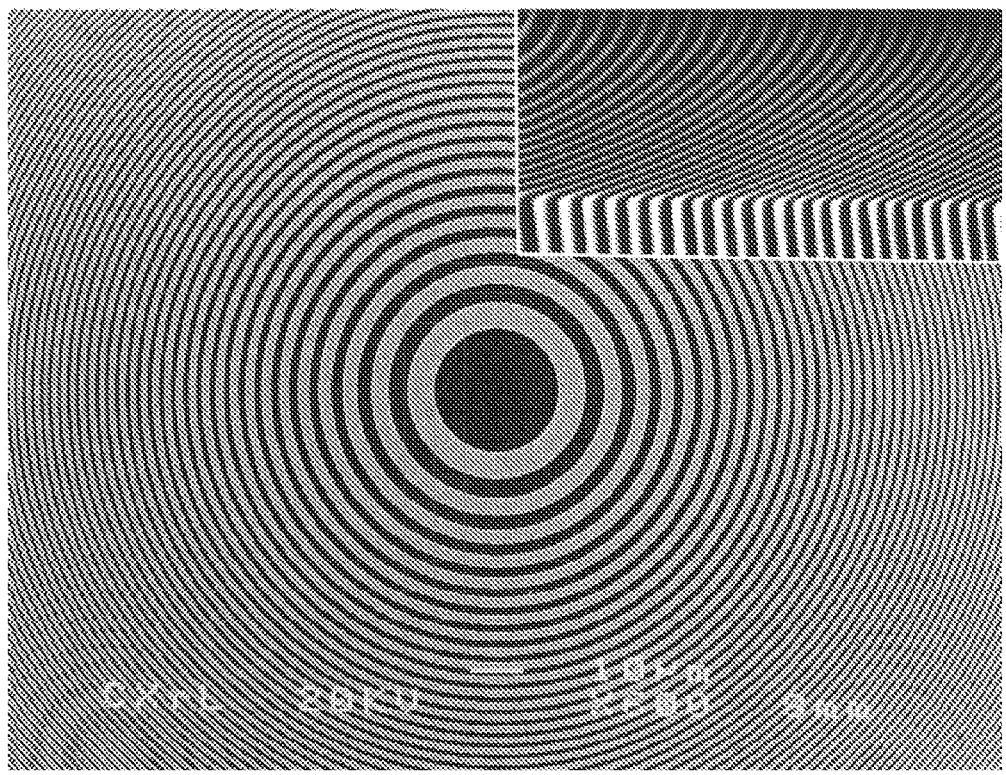
FIG. 1 shows a schematic illustration of a zone plate lens.
Figure 2:
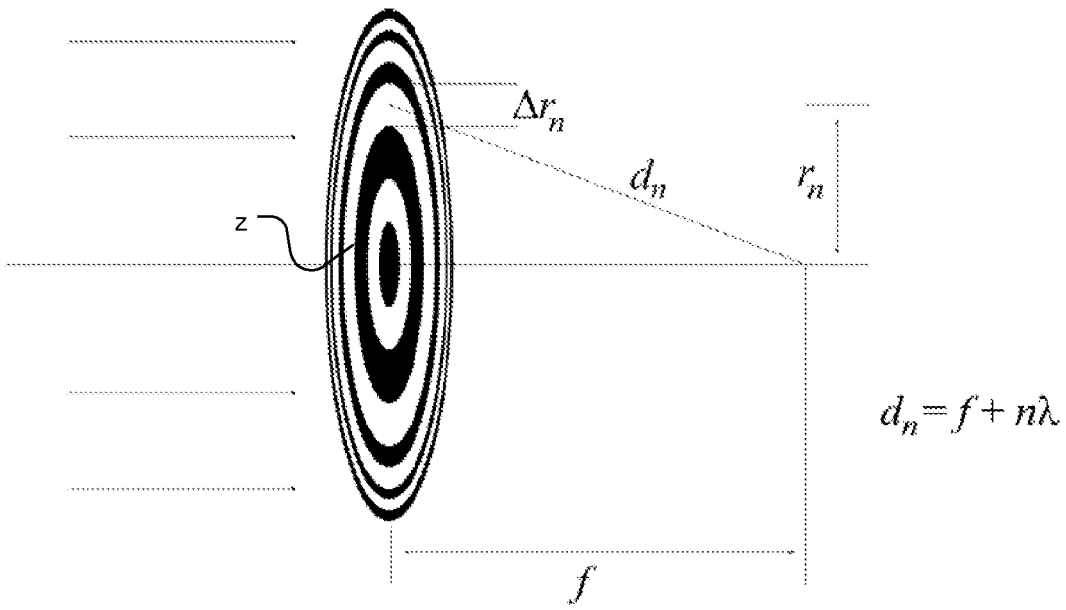
FIG. 2 shows the important characteristics governing the performance of a zone plate lens.
Figure 3:
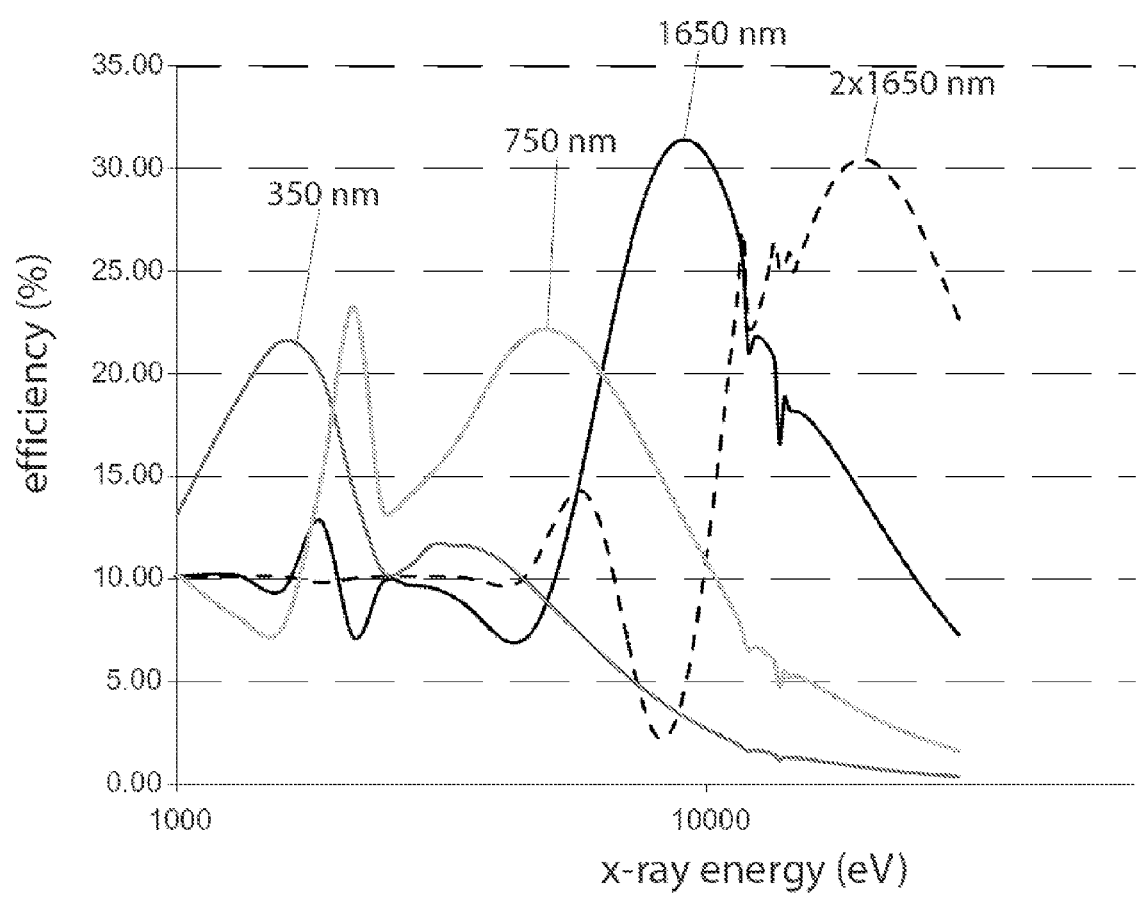
FIG. 3 is a plot of the theoretical efficiency curves of a gold zone plate for lenses of several thicknesses as a function of x-ray energy.
Figure 4:
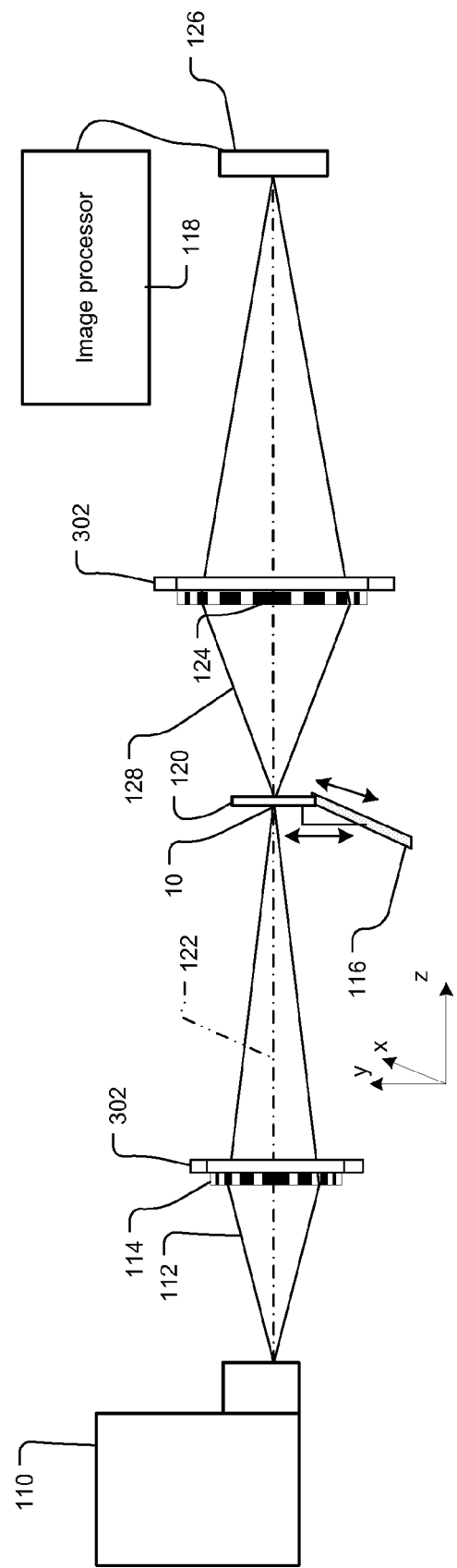
FIG. 4 is a schematic side view of a x-ray imaging system.

FIG. 4 shows an x-ray imaging system that has been constructed according to the principles of the present invention.

The system has an x-ray source 110 that generates an x-ray beam 112 along the optical axis 122. In the current embodiment, the source is a beamline of a synchrotron x-ray generation facility. In other embodiments, lower power sources are used, such as laboratory sources. Such sources often generate x-rays by bombarding a solid target anode with energetic electrons. Specific examples include microfocus x-ray sources and rotating anode sources.

The x-ray beam 112 is preferably a hard x-ray beam. In one embodiment, its energy is about 10 keV. Generally, the beam's energy is between about 2 keV and 25 keV. These higher energies ensure good penetration through any intervening coating, e.g. fluid layer, on the sample 10.

The condenser 114 collects and focuses the x-ray beam 112 from the source 110. For the full field imaging setup, a suitable illumination of the sample 10 is required. This is most conveniently achieved by the use of a zone plate condenser optic 114.

A sample holder 120 is used to hold the sample 10 in the x-ray beam 112. The stage 116 scans the sample holder 120 in both the x and y axis directions, i.e., in a plane that is perpendicular to the axis 122 of the x-ray beam 112. In other examples, the stage 116 further rotates the sample 10 to obtain projections at different angles, which are often used for tomographic reconstruction in an image processor 118.

An x-ray objective 124 collects transmitted x-rays 128. The x-ray beam 128 from the sample 10 is focused onto a detector system 126. In a current embodiment, the objective 124 is a Fresnel zone plate.

The detector system 126 is preferably a high-resolution, high-efficiency scintillator-coupled CCD (charge coupled device) camera system for detecting x-rays from the sample 10. But other x-ray detectors, such as optical taper-based systems can also be used. In one example, a camera system as described in U.S. Pat. No. 7,057,187, which is incorporated herein by this reference in its entirety, is used. The following specific parameters ensure good performance:

Quantum detection efficiency >70% at 10 keV;
Pixel resolution element on scintillator 0.65 μm;
Spatially resolved (1 k×1 k elements in an two dimensional array) CCD detector, Peltier-cooled.

According to embodiments of the invention either the condenser 114 or the x-ray objective 124, or both, is a compound zone plate. In a current embodiment, however, the condenser 114 is a reflective capillary optic and only the objective is a compound zone plate.

FIG. 5A illustrates the construction of the compound zone plate of the condenser 114 and/or objective 124 according to the preferred embodiment of the present invention.

The compound zone plate 114, 124 is held on a holder 302. The holder 302 as an annular shape with a center optical port 350. In the typical implementation, this center optical port 350 has a circular shape when observed looking along the direction of the optical axis 122.

A bottom base frame 304 is secured on to the holder 302. The bottom base frame 304 similarly has a center optical port 352 that is aligned over the optical port 350 of the holder 302. The optical port 352 of the bottom base frame 304 is preferably square shaped when observed along the direction of the optical axis 122. It also has, preferably, obliquely angled sidewalls 354 such that the port 352 has a frusto-pyramidal profile. In the preferred embodiment, the bottom base frame 304 is constructed from silicon wafer material and has a isosceles trapezoidal cross sectional profile. The angled sidewalls 354 are fabricated by silicon anisotropic etching of the wafer material.

A first small frame zone plate 310 is secured to the bottom base frame 304. The small frame zone plate 310 comprises an outer frame 358 that has an isosceles trapezoidal cross sectional profile. A frusto-pyramidal center optical port 356 is formed in the outer frame 358 and aligned on the optical axis 122. Preferably the outer frame 356 is fabricated from silicon wafer material. Preferred thicknesses range from 100 to 500 micrometers. It is currently approximately 180 micrometers thick.

Extending over the center optical port is a membrane 360, which currently constructed from silicon nitride. In other embodiments, the membrane 360 is constructed from silicon carbide, silicon, silicon oxide, or diamond (carbon). Its thickness is typically between 0.05 to 2 micrometers. It is currently about 0.1 to 0.3 micrometers thick. A zone plate structure 312a is disposed on the membrane 360 and centered along the optical axis 122.

The first small frame zone plate 310 is secured to the bottom base frame 304 via an adhesive layer 308. Small microbeads 306 in the adhesive layer 308 separate the outer frame 358 from the top surface of the bottom base frame 304 providing a controlled the spacing between these two elements. In the current embodiment, the microbeads are silicon oxide because of the hardness, quality of available beads, and close thermal matching to the silicon frames.

A first large frame zone plate 316 is also secured to the top surface of the bottom base frame 304. Similar to the small frame zone plate 310, the large frame zone plate 316 comprises an outer frame 358 having an isosceles trapezoidal cross sectional profile with a frusto-pyramidal center optical port 356. This center optical port 356, however, is sized to accommodate, i.e., be larger than, the overall diameter of the first small frame zone plate 310 such that the first small frame zone plate 310 fits entirely, laterally, within the center optical port 356 of the large frame zone plate 316.

The first large frame zone plate 316 includes a membrane 360 that extends over its center optical port 356 and the width of the small frame zone plate 310. A second zone plate 312b is formed on the top of the membrane 360 of the large frame zone plate 316.

The outer frame 358 of the first large frame zone plate 316 is secured to the top surface of the base frame 304 via an adhesive layer 308. Large spherical microbeads 314 mixed in the adhesive layer 308 are located between the bottom surface of the outer frame 358 of the first large frame zone plate 316 and the top surface of base frame 304 to provide a controlled distance between these two elements. The large bead 314 ensure adequate clearance between the underside of the membrane 360 of the first large frame zone plate 316 and the top of zone plate 312a.

A second large frame zone plate 318 is installed on the first large frame zone plate 316. It is an orientation, however, is inverted such that zone plate 312c formed on the membrane of the second large frame zone plate 318 is directly opposite the zone plate 312b of the first large frame zone plate 316.

The second large frame zone plate 318 is secured to the first large frame zone plate 316 via an adhesive layer 308. Medium spherical microbeads 319 in layer 308 to define a standoff distance between the top surface of the first large frame zone plate 316 and the bottom surface of the second large frame zone plate 318. The medium microbeads 319 ensure that zone plate 312b is separated from zone plate 312c to prevent damage.

A subassembly is constructed from a top base frame 320 and a second small frame zone plate 322. In more detail, the top base frame 320, similar to the bottom base frame 304, includes a center frusto-pyramidal optical port 352. It further has an isosceles trapezoidal cross sectional profile. A second small frame zone plate 322 is secured over this optical port 352. The second small frame zone plate 322 is constructed in a similar fashion to the first small frame zone plate 358. It includes a center frusto-pyramidal optical port 356 that is formed in a outer frame 358. A membrane 360 extends over the optical port 356. A zone plate 312d is fabricated on this membrane 360.

The second small frame zone plate 322 is secured to the top base frame 320 such that their respective optical ports are aligned with each other. They are bonded together using an adhesive layer 308. Small spherical microbeads 306 are used to define the standoff distance between the top base frame 320 and the second small frame zone plate 322.

The subassembly comprising the top base frame 320 and the second small frame zone plate 322 is inverted and bonded onto the top surface of the second large frame zone plate 318. They are secured by an adhesive layer 308. Large microbeads 314 in the layer 308 are used to set the distance between the bottom surface of the top base frame 320 and the top surface of the second large frame zone plate 318.

In the preferred embodiments, the construction and sizing of the large frame zone plates 316, 318 and the small frame zone plates 310, 322 are similar. That is, preferably they are all constructed from silicon wafer material with a thickness ranging from 100 to 500 micrometers, currently approximately 180 micrometers thick. The membranes 360 are currently silicon nitride, but silicon carbide, silicon, silicon oxide, or diamond are other examples. The membrane thickness is typically between 0.05 to 2 micrometers. It is currently about 0.1 to 0.3 micrometers thick.

The total overall distance 324 of the four zone plates 312a, 312b, 312c, 312d measured along the optical axis 122 is critical to high performance operation and should be minimized, to preferably less than the depth of focus of the zone plates 312a, 312b, 312c, 312d. Using typical numerical apertures (NA) in the range from 0.5 mrad to 8 mrad and for wavelengths from 0.05 nm to 0.25 nm. The DOF maximally ranges from 0.8 um to 250 um. Thus the distance 324 should be between 0.8 micrometers to 250 micrometers depending on the wavelength used. Currently, the DOF is more restricted from 10-100 micrometers, thus, in the current embodiment distance 324 is between 10-100 micrometers.

In one embodiment, where the four zone plates 312a, 312b, 312c, 312d nominally have identical geometry, including diameter and outer zone width. That is, they have the same geometry, including diameter and outer zone width within manufacturing tolerances. In other embodiments, the four zone plates 312a, 312b, 312c, 312d form two four-step blazed zone plates or one 16-step blazed zone plate as described below.

FIG. 5A illustrates the construction of the compound zone plate of the condenser 114 and/or objective 124 according to another embodiment.

This example includes only to zone plates 312a, 312b. It is fabricated attaching two zone plate frames 310, 322 to each other. A layer of adhesive 308 is used to bond the zone plate frames 310, 322. A layer of microbeads 319 in the adhesive defines the standoff distance and prevents damage to the zone plates 312a, 312b due to contact.

FIGS. 6A through 6F illustrate the process for fabricating the zone plates 312a-d on the frames 310, 316, 318, and 322. The method for fabricating the framed zone plates is essentially similar for the large frames 316, 318 and the small frames 310, 322. The only difference is the lateral overall size of the frames and their center frusto-pyramidal optical ports 352.

Figure 6A:
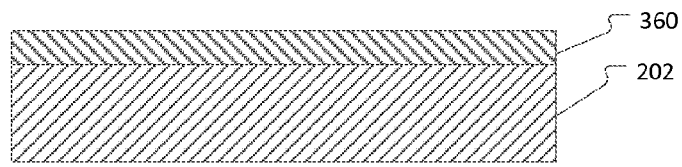
FIG. 6A through 6G illustrate a process for fabricating the zone plates on the frames.

As shown in FIG. 6A, the process begins with silicon wafer material 202 with an <100> crystalline orientation. A top silicon nitride membrane layer 360 is deposited on the wafer material 202.

Figure 6B:
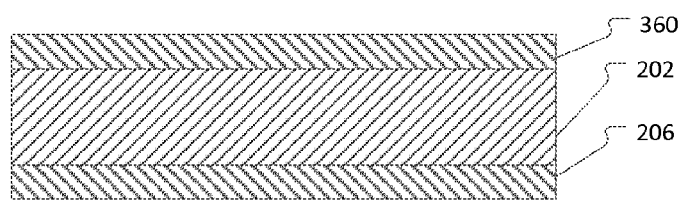

In FIG. 6B, a bottom silicon nitride layer 206 is deposited on the opposite side of the wafer material 202. This second silicon nitride layer 206 has typically the same thickness as the top layer.

Figure 6C:
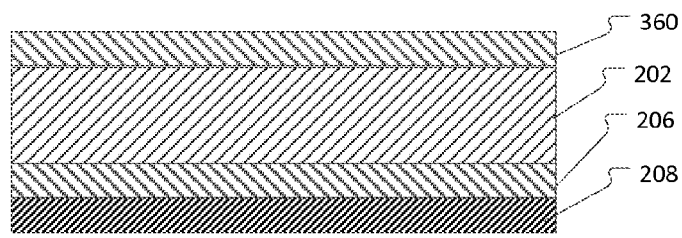
Figure 6D:
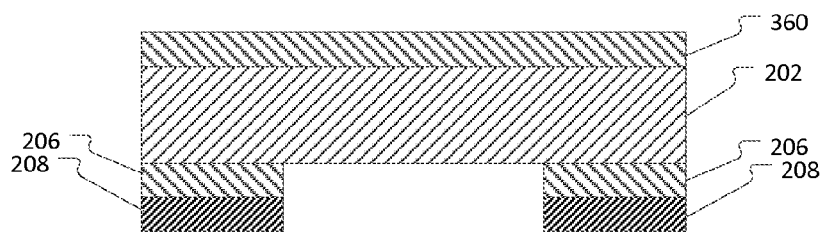

As shown in FIGS. 6C and 6D, a photoresist is then deposited on the bottom silicon nitride layer 206 and then patterned to the approximate desired size of the optical port. The exposed portions of the bottom silicon nitride layer 206 are then removed.

Figure 6E:
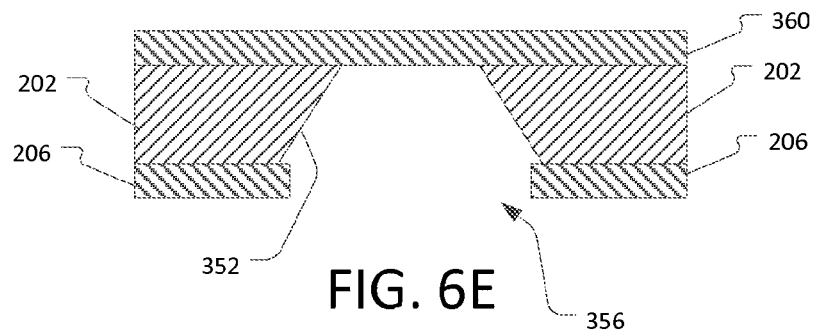

An anisotropic etch process is then performed on the exposed wafer material 202 as shown in FIG. 6E. In a preferred embodiment, a KOH wet etch process is used. This preferentially etches the <100> crystalline lattice. It thus forms sloped side walls corresponding to the <111> plane of the wafer material 202. The etch is performed to the depth of the top silicon nitride layer 204 to form the membrane 360.

Figure 6F:
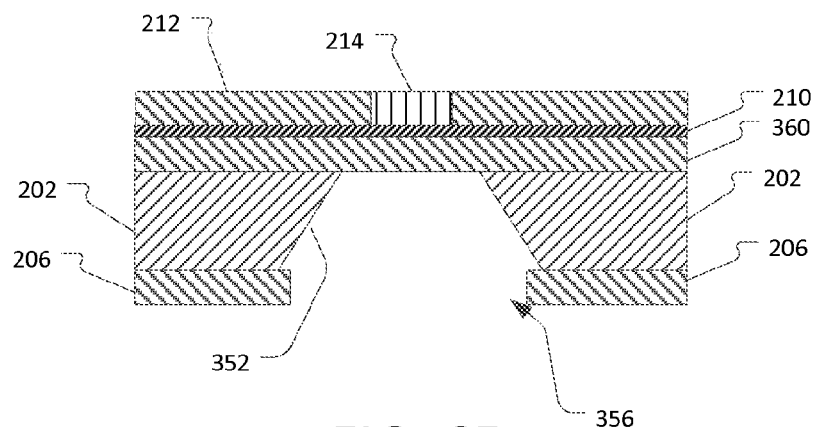

FIG. 6F illustrates the conventional processing performed on the front side. In more detail, a thin metal seed layer 210 is deposited on the top silicon nitride membrane layer 360. A photoresist layer 212 is deposited on the metal layer. This is patterned 214 with the reverse pattern for the zone plate. And for embodiment, this patterning is performed by an electron beam writer. The pattern typically gets transferred to a thin metal layer, not shown, and then deep transferred into the polymer resist. Into this reverse pattern, the structure of the zone plate is plated beginning at the seed layer 210.

Figure 6G:
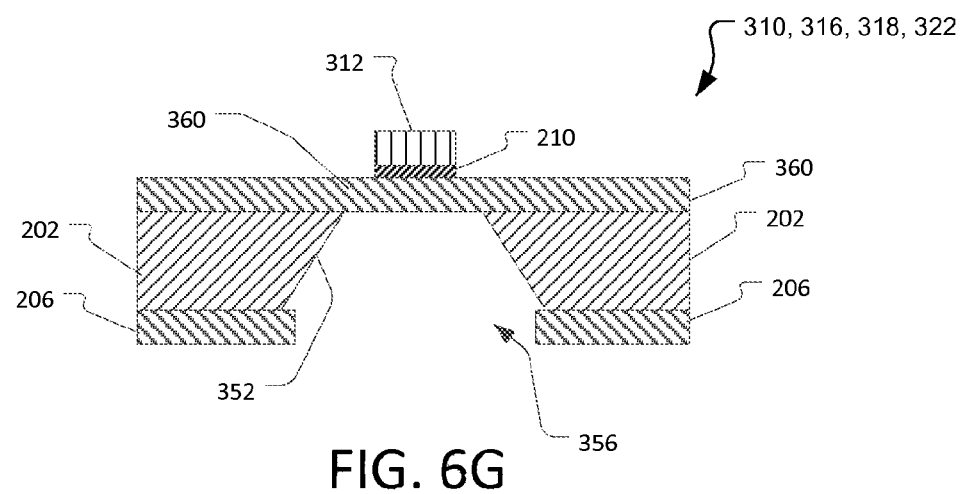

As illustrated in FIG. 6G, after the plating step, the photoresist layer 212 is stripped leaving the plated structure of the zone plate 312.

It should be noted that material stress control is important. Generally, when moving to a thicker membrane layer 360, from 0.3 micrometers to 1.0 micrometers, the stress in the membrane distorted the zone plates 312 on the large frames, so that the zone plates could not be aligned to each other. Thus, material stress in the membrane layer should be reduced or thinner membranes used.

FIG. 7A through 7E illustrate the process for assembling the zone plate frames 310, 316, 318, 322 into the compound zone plate 114, 124. The general process includes the assembly of a zone plate doublet. Typically, two zone plate frames are then bonded successively to make the compound zone plate comprising the four separate zone plates.

In the assembly process, a combination an adhesive and microbeads or microspheres are used between zone plate frames and based frames. These microspheres or microbeads (1) ensure the parallelism (2) dial in the distance precisely between the zone plates (3) ensure low friction lateral movement enabling nm-precision alignment of the zone plates with respect to each other prior to being fixed by the adhesive. That is, when the frames are pressed together to ensure parallelism, it is still possible to align them to each other since the microbead layer facilitates the inplane movement of the alignment process. In general, three different size classes of microbeads are used in the process described below. In other examples, one a single size is used. In any event, and in general, the microbeads in the size range of 0.5 to 10 micrometers. Currently, microbeads in the range of 1.6 to 10 micrometers are being used.

Figure 7A:
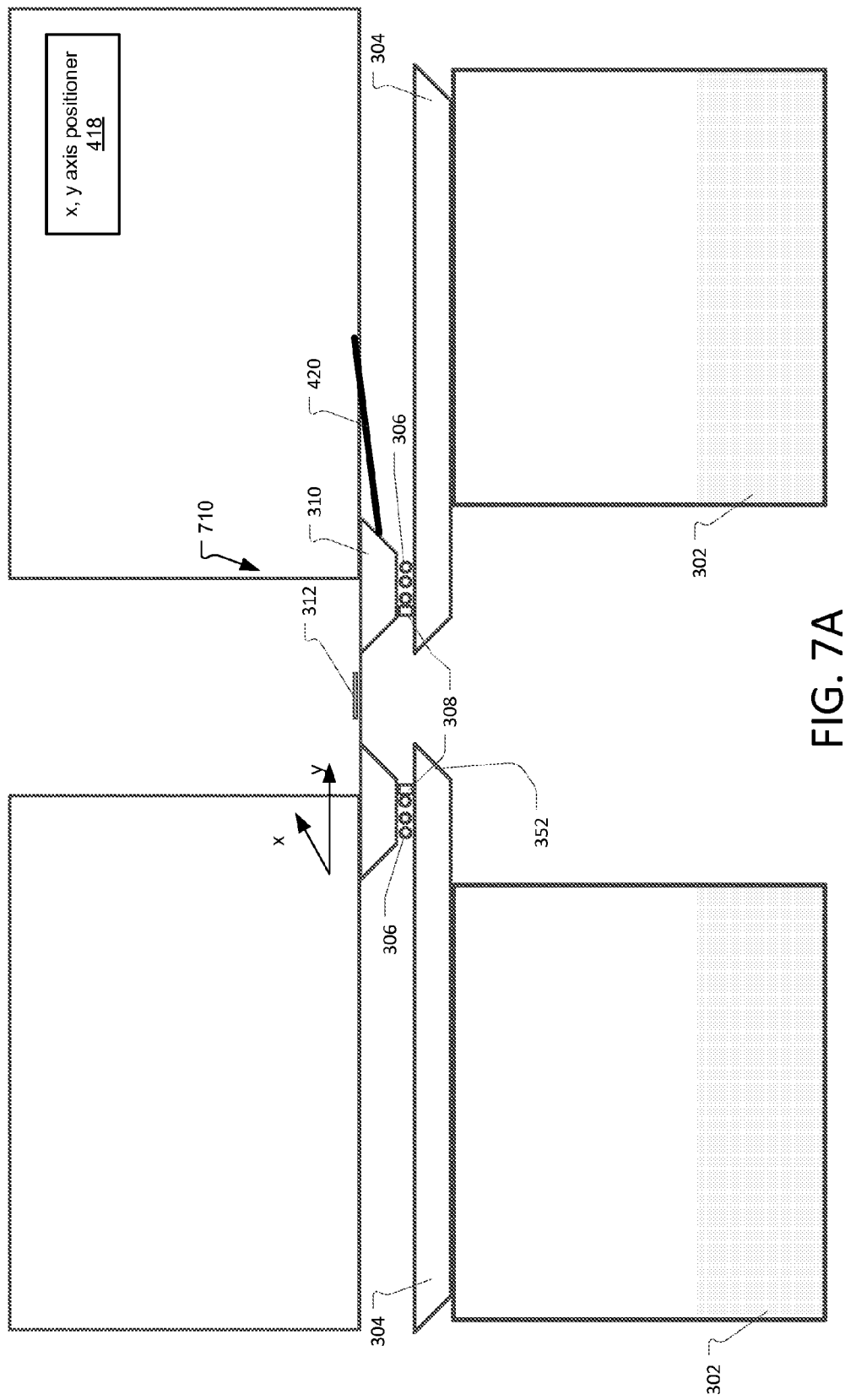
FIG. 7A through 7E illustrate the process for assembling the zone frames into the compound zone plate.

FIG. 7A shows the bonding of the small frame zone plate 310 onto the bottom base frame 304 to create assembly 710. As described previously, they bonded together using an adhesive layer 308. Small spherical microbeads 306 used to precisely control the standoff distance between the top surface of the bottom base frame 304 and the bottom surface of the small frame zone plate 310, in some implementations.

The alignment between the bottom base frame 304 and the small frame zone plate 310 is a relatively coarse alignment. That is, the zone plate 312 need only be generally centered on the center optical port 352 of the bottom base frame 304. Typically this alignment is performed using a standard stereo microscope. The adhesive 308 is applied between the bottom base frame 304 and the small zone plate 310. A precision x, y axis positioner 418 is used to first position and then hold the small frame zone plate 310 in position while the adhesive 308 cures. The x, y axis positioner 418 also provides a downward force by a spring mechanism to push the first small frame zone plate 310 against the bottom base frame 304 to ensure good contact and maintain planarity.

A compound lens assembly is sensitive to angular deviations. For example, a 3-degree tilt will cause 50 nm lateral shift in the relative zone position. For a zone plate element with 50 nm outer zone width, this shift will be the same as the zone width—thus render the compound zone plate unusable. The downward force applied by the positioner 418 ensures parallelism and spacing.

Figure 7B:
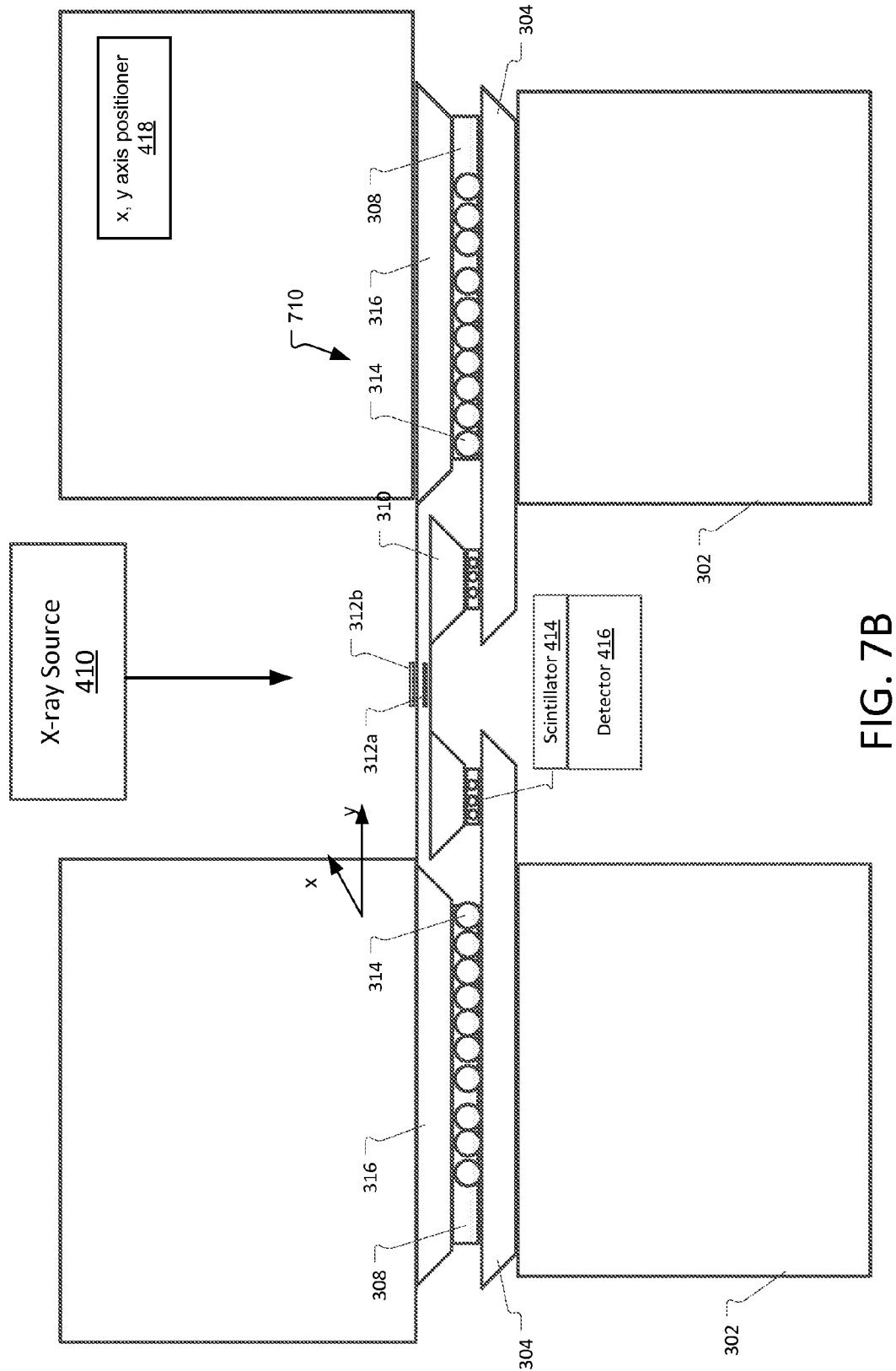

FIG. 7B illustrates the attachment of the first large frame zone plate 316 to the bottom base frame 304. Again, adhesive 308 is applied between the bottom surface of the first large frame zone plate 316 and the bottom base frame 304. Large spherical microbeads 314 are deposited between the large frame zone plate 316 and the bottom base frame 304 to ensure a precision standoff distance.

The lateral alignment between zone plate 312b and a zone plate 312a must be as accurate as possible. In the preferred embodiment, an active alignment process is used. Ideally, the alignment is performed using feedback from the transmission of x-rays through the zone plates 312a and 312b.

In more detail, a microfocus x-ray source 410 generates an x-ray beam that illuminates the zone plates 312a and 312b. Preferably, the x-ray source 410 generates x-rays having an energy of a system in which the compound zone plate 114, 124 will be deployed. The x-rays are transmitted through the zone plates 312a and 312b and converted into the optical frequencies by a scintillator 414, if required. A spatially resolved CCD detector 416, comprising a two dimensional array of pixels, detects the two dimensional pattern produced by the zone plates 312a and 312b.

The x, y axis positioner 418 is then controlled to position the large frame zone plate 316 relative to the small frame zone plate 310 in the x and y axes based on the x-ray focus intensity or interference pattern detected by the detector 416. Currently the alignment is performed based on the Moire pattern formed on the detector 416. The microbeads 314 facilitate this positioning process by providing a low stiction mechanical interface. Once the optimal position is discovered the x, y axis positioner 418 holds that position while pushing down on the first large frame zone plate 316 to ensure good mechanical contact, parallelism and planarity relative to the bottom base frame 304, which is functioning as the mechanical reference, until the adhesive 308 cures. Currently a two part slow curing epoxy is used to facilitate the alignment process.

Figure 7C:
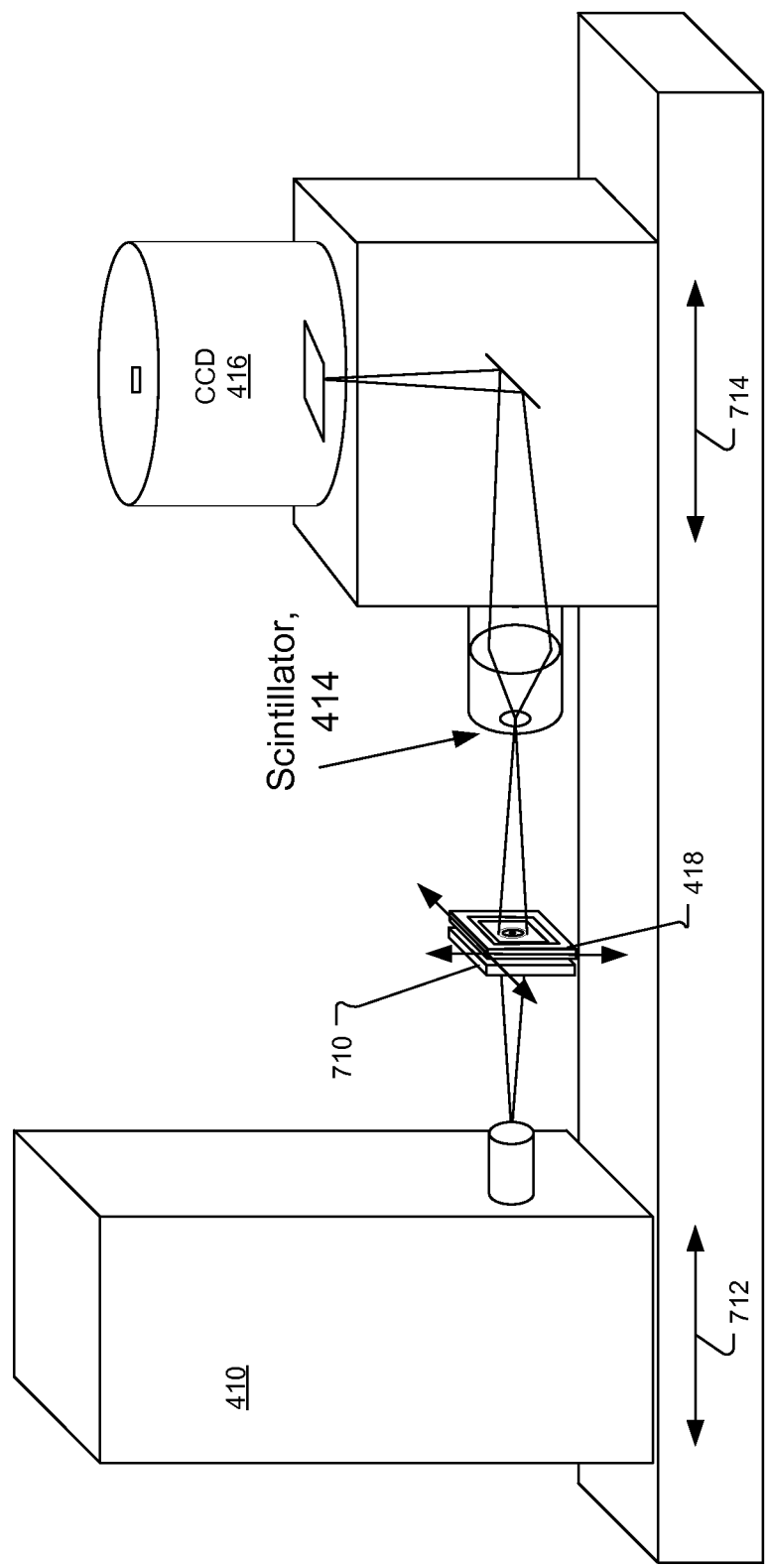

FIG. 7C shows the x-ray system used for alignment. The x-ray source 410 generates a beam that is transmitted through the assembly 710. The positioning urges the next frame into engagement with the assembly while position that frame in the plane of the assembly. This positioning is performed in response to the pattern formed on the CCD detector 416.

To improve that clarity of the Moire pattern detected by the CCD 416, both the source 410 and the detector assembly are moved on an optical bench relative to the positioner 418, see arrows 712, 714.

Figure 7D:
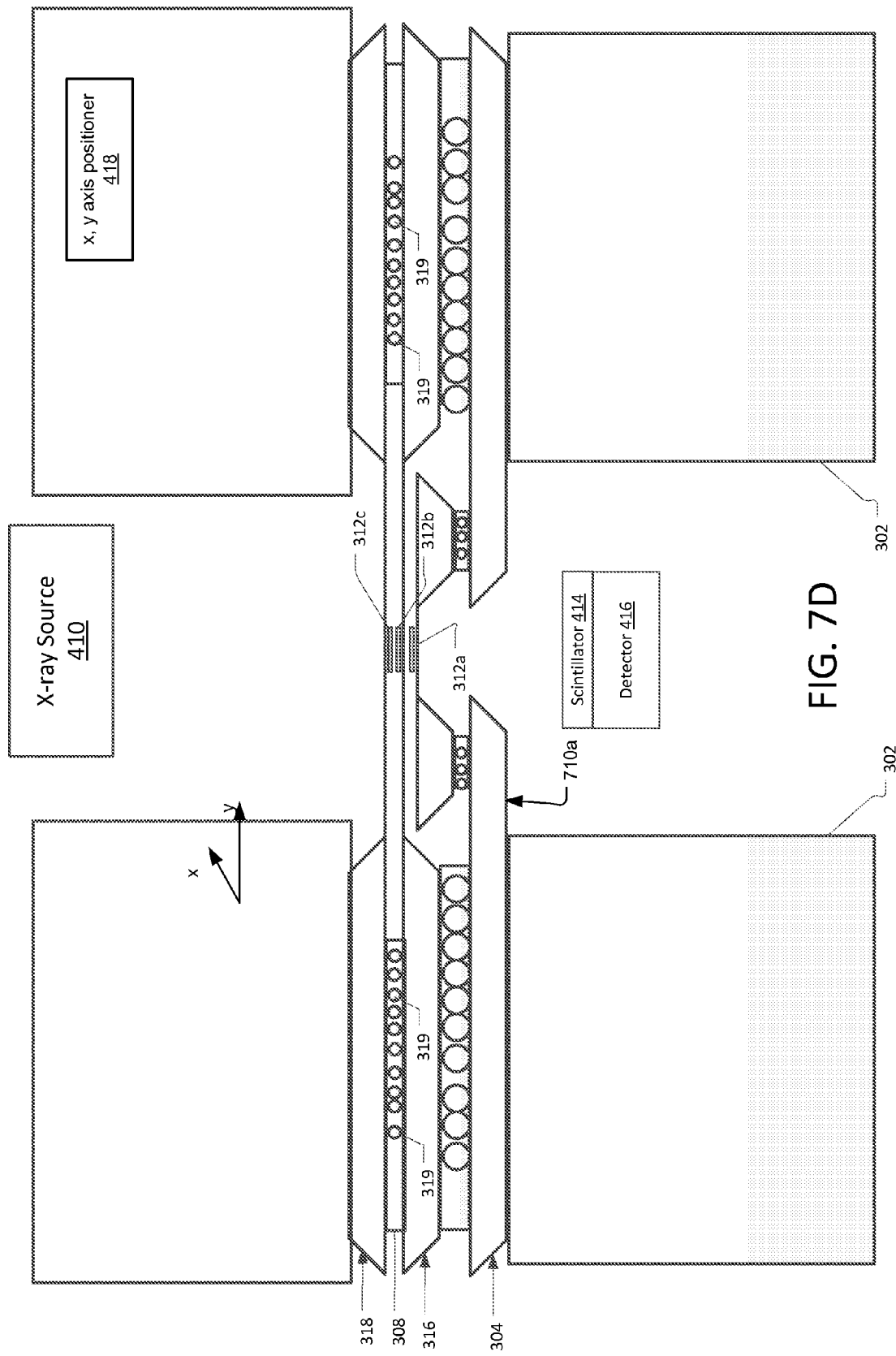

As shown in FIG. 7D, the process is repeated for the attachment of the second large frame zone plate 318 to the top of the first large frame zone plate 316. Again, the x-ray focus intensity or interference pattern detected by the detector 416 is used to align zone plate 312c to the zone plate doublet comprising zone plates 312a and 312b. The microbeads 319 facilitate this positioning process by providing a low stiction interface to allow the x, y axis positioner 418 to move the second large frame zone plate 318.

Note: when fabricating the dual zone plate compound zone plate shown in FIG. 5B, the bonding step as described in FIG. 7D is performed. The main difference is that in the fabrication of this embodiment, the first small frame zone plate 310 is not used. Further, the microbeads between the first large frame zone plate 316 and the bottom base frame 304 are not always used.

Figure 7E:
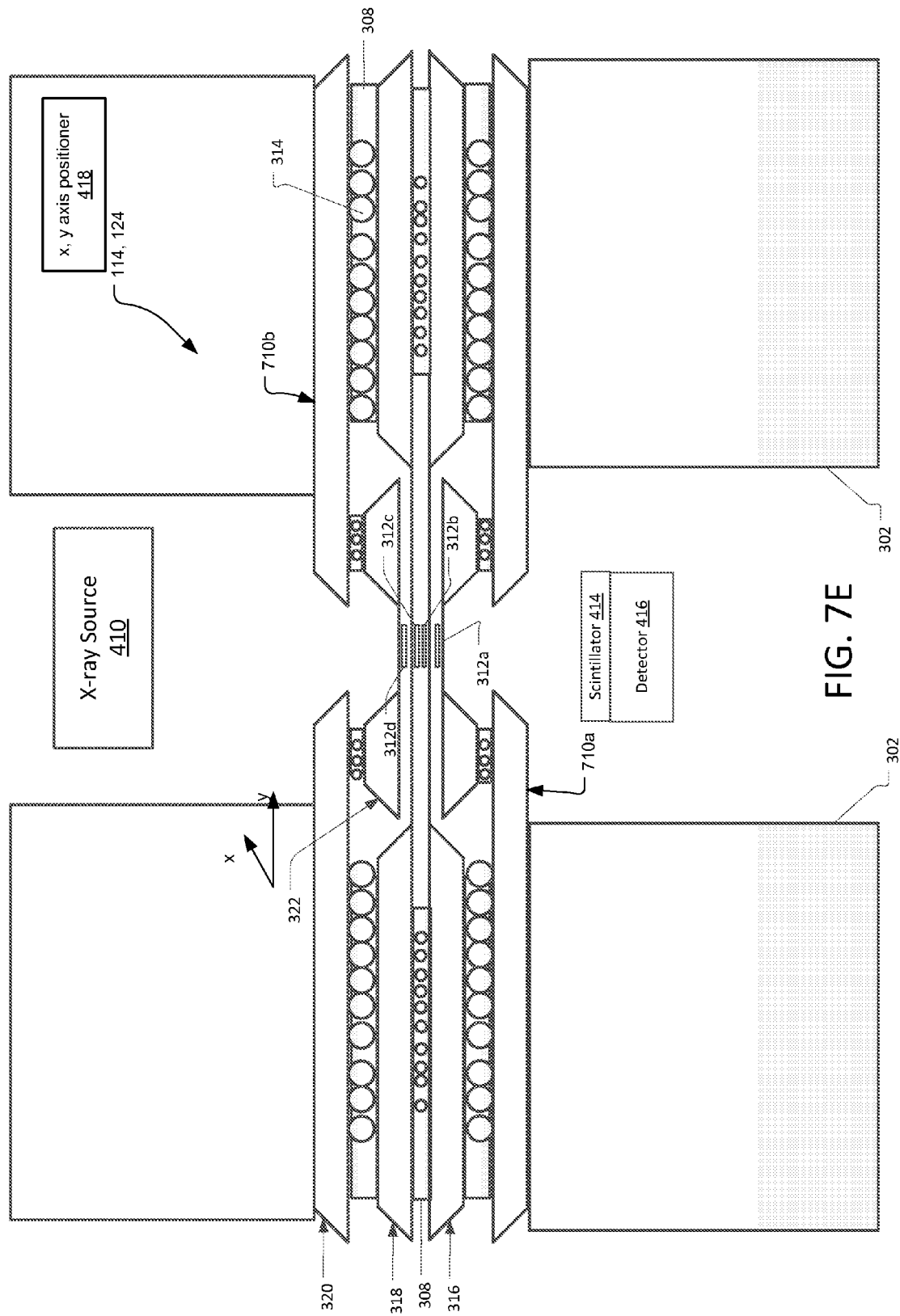

Finally, as shown in FIG. 7E, the process is repeated for the attachment of a sub assembly comprising the top base frame 320 and the second small frame zone plate 322 to the top surface of the second large frame zone plate 318. The x-ray focus intensity or interference pattern produced by the detector 416 is used to align zone plate 312d to the zone plate series comprising zone plates 312a, 312b, 312c. The microbeads 314 facilitate this positioning process, allowing the x, y axis positioner 418 to move the sub assembly comprising the top base frame 320 and the second small frame zone plate 322 for the alignment in a low stiction environment.

In the assembly process, up to three size classes of microbeads may be used: small, medium and large. Finer sized gradations are used in some instances to compensate for variations in the silicon frame thicknesses.

In one embodiment, a blazed zone plate with stepped profile is fabricated by stacking two zone plates with different zone spacing as shown in FIG. 8. In this example, one zone plate 312a has double the spacing of zones 150 with respect to the zones 152 of the other zone plate 312b. When they are stacked in to a compound lens, a stepped profile approximating a Fresnel lens shape is created as shown in FIG. 9. Furthermore, additional zone plates can be used to produce better approximation of the Fresnel lens shape. In general $2^n$ steps can be created by stacking n zone plates elements.

A compound lens assembly as shown in FIGS. 5A and 5B can be very sensitive to angular deviations during use. For example, if a spacer is 1 um thick, a 3-degree tilt will cause 50 nm lateral shift in the relative zone position. For a zone plate element with 50 nm outer zone width, this shift will be the same as the zone width—thus render the compound zone plate unusable. Therefore a compound lens assembly is preferably integrated with an angular adjustment device, such as a tip-tilt stage.

While this invention has been particularly shown and described with references to preferred embodiments thereof, it will be understood by those skilled in the art that various changes in form and details may be made therein without departing from the scope of the invention encompassed by the appended claims. For example, while the description illustrate the fabrication of compound zone plates with 2 and 4 zone plate elements, the principles and technology described here is extendable to compound zone plates with 3 and more than four zone plate elements.

What is claimed is:

1. A method for fabricating a compound zone plate comprising:
   placing a first zone plate frame comprising a first zone plate over a second zone plate frame comprising a second zone plate;
   placing microbeads and an adhesive mechanically between the first zone plate frame and the second zone plate frame; and
   aligning the first zone plate to the second zone plate prior to hardening of the adhesive by using the microbeads to facilitate inplane relative movement between the first zone plate and the second zone plate.

2. A method as claimed in claim 1, wherein the step of aligning the first zone plate to the second zone plate comprises:
   bonding the first zone plate frame to a base frame; and
   bonding the second zone plate frame to the base frame, wherein the base frame is a reference plane used for aligning the first zone plate relative to the second zone plate.

3. A method for fabricating a compound zone plate comprising:
   placing a first zone plate frame comprising a first zone plate over a second zone plate frame comprising a second zone plate;
   placing microbeads and an adhesive mechanically between the first zone plate frame and the second zone plate frame; and
   aligning the first zone plate to the second zone plate prior to hardening of the adhesive by transmitting x-rays through the first zone plate and the second zone plate and detecting the x-rays and positioning the first zone plate relative to the second zone plate in response to the detected x-rays.

4. A method as claimed in claim 3, wherein the x-rays are detected with a spatially resolved detector.

5. A method for fabricating a compound zone plate comprising:
placing a first zone plate frame comprising a first zone plate over a second zone plate frame comprising a second zone plate;
placing microbeads and an adhesive mechanically between the first zone plate frame and the second zone plate frame;
aligning the first zone plate to the second zone plate prior to hardening of the adhesive; and
aligning a third zone plate to the first zone plate and the second zone plate.

6. A method as claimed in claim 5, further comprising aligning a fourth zone plate to the first zone plate, the second zone plate, and the third zone plate.

7. A method for fabricating a compound zone plate comprising:
placing a first zone plate frame comprising a first zone plate over a second zone plate frame comprising a second zone plate;
placing microbeads and an adhesive mechanically between the first zone plate frame and the second zone plate frame;
aligning the first zone plate to the second zone plate prior to hardening of the adhesive; and
wherein different sized microbeads are used in the adhesive between a base frame and the first zone plate frame relative to the adhesive between the base frame and the second zone plate frame to control a relative spacing of the zone plate frames with respect to each other.

8. A method for fabricating a compound zone plate comprising:
placing a first zone plate frame comprising a first zone plate over a second zone plate frame comprising a second zone plate;
placing microbeads and an adhesive mechanically between the first zone plate frame and the second zone plate frame;
aligning the first zone plate to the second zone plate prior to hardening of the adhesive;
placing a third zone plate frame comprising a third zone plate over the second zone plate frame; and
placing microbeads and adhesive mechanically between the second zone plate frame and the third zone plate frame.

9. A method as claimed in claim 8, further comprising:
bonding a fourth zone plate frame comprising a fourth zone plate to a base frame and then placing the base frame on the third zone plate frame; and
placing microbeads and adhesive mechanically between the base frame and the third zone plate frame, wherein the base frame is a reference plane used for aligning the zone plates relative to each other.

10. A method for fabricating a compound zone plate comprising:
bonding a first zone plate frame comprising a first zone plate over a second zone plate frame comprising a second zone plate; wherein the first zone plate frame and the second zone plate frame are bonded on a base frame and wherein the second zone plate frame comprises an optical port and the first zone plate frame is situated at least partially within the optical port of the second zone plate frame.

11. A method as claimed in claim 10, further comprising using a spacer between the first zone plate frame and the base frame.

12. A method as claimed in claim 10, further comprising fabricating the second zone plate frame on a membrane, and fabricating an optical port into the first zone plate frame to produce an unsupported membrane over the optical port.

13. A method as claimed in claim 12, further comprising positioning the first zone plate laterally within the optical port.

14. A method as claimed in claim 10, further comprising bonding a third zone plate frame comprising a third zone plate to the second zone plate frame.

15. A method as claimed in claim 14, further comprising inserting a spacer between the second zone plate frame and the third zone plate frame.

16. A method as claimed in claim 14, further comprising bonding a fourth zone plate frame to an additional base frame and subsequently bonding the additional base frame to the third zone plate frame.

17. A method for fabricating a compound zone plate comprising:
bonding a first zone plate frame including a first zone plate over a base frame;
placing a second zone plate frame including a second zone plate over the base frame;
inserting a spacer between the base frame and the second zone plate frame, wherein the spacer includes microbeads; and
aligning the first zone plate to the second zone plate by using the microbeads to facilitate inplane relative movement between the first zone plate and the second zone plate.

18. A method for fabricating a compound zone plate comprising:
bonding a first zone plate frame comprising a first zone plate over a base frame;
bonding a second zone plate frame comprising a second zone plate over the base frame;
positioning and holding the base frame with respect to the first and second zone plate frames with an x, y axis positioner; and
aligning the first zone plate to the second zone plate by using the microbeads to facilitate inplane relative movement between the first zone plate and the second zone plate.

19. A method as claimed in claim 18, wherein the aligning of the first zone plate to the second zone plate is based on feedback from x-rays that are transmitted through the first zone plate and the second zone plate.

* * * * *